United States Patent
Pimont-Garro et al.

(10) Patent No.: US 9,115,108 B2
(45) Date of Patent: Aug. 25, 2015

(54) SALT OF ABEXINOSTAT, ASSOCIATED CRYSTALLINE FORM, A PROCESS FOR THEIR PREPARATION AND PHARMACEUTICAL COMPOSITIONS CONTAINING THEM

(71) Applicants: LES LABORATOIRES SERVIER, Suresnes Cedex (FR); PHARMACYCLICS, Sunnyvale, CA (US)

(72) Inventors: Anne Pimont-Garro, Versailles (FR); Philippe Letellier, Orleans (FR)

(73) Assignee: PHARMACYCLICS, INC., Sunnyvale, CA (US)

( * ) Notice: Subject to any disclaimer, the term of this patent is extended or adjusted under 35 U.S.C. 154(b) by 0 days.

(21) Appl. No.: 14/195,186

(22) Filed: Mar. 3, 2014

(65) Prior Publication Data

US 2014/0249215 A1 Sep. 4, 2014

Related U.S. Application Data

(60) Provisional application No. 61/772,191, filed on Mar. 4, 2013.

(30) Foreign Application Priority Data

Mar. 4, 2013 (FR) ..................... 13 51898

(51) Int. Cl.
*C07D 307/85* (2006.01)
*C07C 309/30* (2006.01)

(52) U.S. Cl.
CPC ............ *C07D 307/85* (2013.01); *C07C 309/30* (2013.01)

(58) Field of Classification Search
USPC .................... 549/468, 467; 514/469
See application file for complete search history.

(56) References Cited

U.S. PATENT DOCUMENTS

| 7,276,612 B2 * | 10/2007 | Verner et al. .................. 549/467 |
| 2014/0057862 A1 * | 2/2014 | Loury et al. .................... 514/34 |
| 2014/0194479 A1 * | 7/2014 | Schmauss et al. ............ 514/357 |

FOREIGN PATENT DOCUMENTS

| WO | WO 2004/092115 | 10/2004 |
| WO | WO 2010/123507 | 10/2010 |

OTHER PUBLICATIONS

French Preliminary Search Report for FR1351898 of Oct. 30, 2013.

* cited by examiner

*Primary Examiner* — Noble Jarrell
*Assistant Examiner* — John Mauro
(74) *Attorney, Agent, or Firm* — Hueschen and Sage

(57) ABSTRACT

Abexinostat tosylate of formula (II):

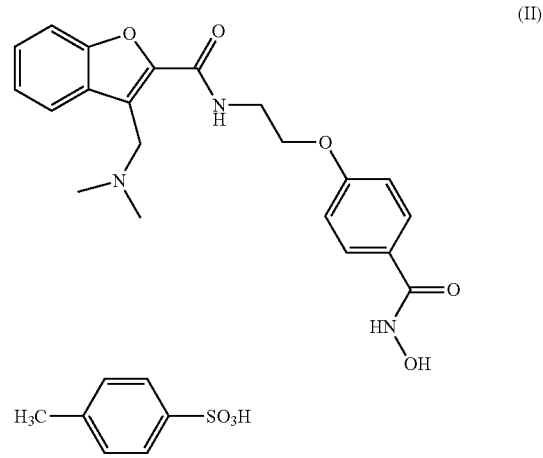

and its crystalline form I characterized by its X-Ray powder diffraction diagram, its Raman spectrum and its solid-state $^{13}C$ CP/MAS NMR spectrum.
Medicinal products containing the same which are useful in the treatment of cancer.

13 Claims, No Drawings

SALT OF ABEXINOSTAT, ASSOCIATED CRYSTALLINE FORM, A PROCESS FOR THEIR PREPARATION AND PHARMACEUTICAL COMPOSITIONS CONTAINING THEM

The present invention relates to N-hydroxy-4-{2-[3-(N,N-dimethylaminomethyl)-benzofuran-2-ylcarbonylamino]ethoxy}benzamide tosylate, or a solvate thereof.

Alternatively, the subject-matter of the invention relates to a tosylate salt of abexinostat of formula (I):

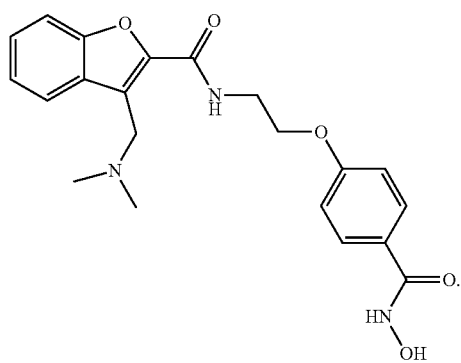

More especially, the invention is directed to the salt of formula (II):

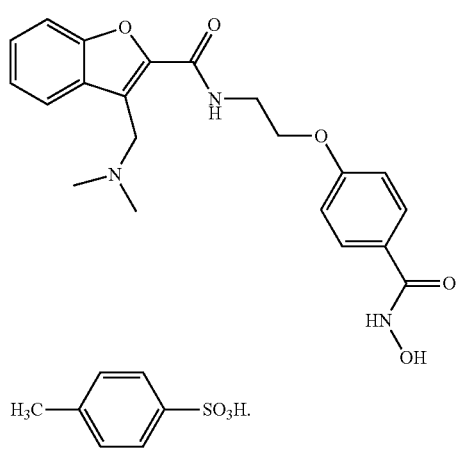

The present invention relates also to crystalline form I of N-hydroxy-4-{2-[3-(N,N-dimethylaminomethyl)benzofuran-2-ylcarbonylamino]ethoxy}benzamide tosylate, to a process for its preparation and also to pharmaceutical compositions comprising it.

N-hydroxy-4-{2-[3-(N,N-dimethylaminomethyl)benzofuran-2-ylcarbonylamino]ethoxy}-benzamide, also known as abexinostat, is a histone deacetylase (HDAC) inhibitor described in patent application WO2004/092115. It allows inhibition of cell growth and induces apoptosis in cultured tumour cells in vitro, and it inhibits tumour growth in vivo in xenograft models (Buggy et al., *Mol. Cancer Ther* 2006 5(5) 1309). In view of its pharmacological profile, abexinostat is intended for use in the treatment of cancer.

From the industrial point of view it is imperative to be able to synthesise the compound with excellent purity, especially in a perfectly reproducible form, having valuable characteristics of dissolution, filtration, drying, ease of formulation and stability allowing its prolonged storage without particular requirements for temperature, light, humidity or oxygen levels.

Patent application WO2004/092115 describes two different routes for obtaining abexinostat. In both cases, 3-methylbenzofuran-2-carboxylic acid is used as starting material, but functionalisation of this central nucleus by the dimethylaminomethyl group in the 3-position is carried out at different stages in the synthesis process, namely before or after coupling of the benzofuran-2-carboxylic acid compound with methyl 4-(2-aminoethoxy)benzoate. Obtaining abexinostat hydrochloride is specifically described in the WO2004/092115 application. However, using this salt on an industrial scale is problematic because of its hygroscopic properties.

The present invention describes a process for obtaining abexinostat tosylate (abexinostat 4-methylbenzenesulfonate) in a well-defined, perfectly reproducible crystalline form having very good stability that is compatible with the industrial constraints of preparation (especially drying) and storage of pharmaceutical compositions.

Crystalline form I of abexinostat tosylate is characterised by an X-ray powder diffraction diagram having the following diffraction lines (Bragg's angle 2 theta, expressed in degrees ±0.2°): 6.50; 9.94; 11.35; 12.33; 14.08; 18.95; 21.08; 27.05. Even more especially, crystalline form I of abexinostat tosylate is characterised by the following diffraction lines: 6.50; 9.94; 11.35; 12.33; 14.08; 18.95; 19.61; 19.96; 21.08; 22.82; 23.61; 27.05.

More specifically, crystalline form I of abexinostat tosylate is characterised by the X-ray powder diffraction diagram hereinbelow, measured using a PANalytical X'Pert Pro MPD diffractometer with an X'Celerator detector and expressed in terms of line position (Bragg's angle 2 theta, expressed in degrees ±0.2°) and interplanar distance d (expressed in Å):

| Line no. | Angle 2-theta (degrees) | Interplanar distance (Å) |
| --- | --- | --- |
| 1 | 6.50 | 13.581 |
| 2 | 9.94 | 8.894 |
| 3 | 11.35 | 7.789 |
| 4 | 12.33 | 7.173 |
| 5 | 14.08 | 6.285 |
| 6 | 18.95 | 4.683 |
| 7 | 19.61 | 4.526 |
| 8 | 19.96 | 4.449 |
| 9 | 21.08 | 4.215 |
| 10 | 22.82 | 3.897 |
| 11 | 23.61 | 3.768 |
| 12 | 27.05 | 3.296 |

Besides that, crystalline form I of abexinostat tosylate has been characterised by Raman spectroscopy. Significant peaks were observed at the following positions: 940 cm$^{-1}$, 1088 cm$^{-1}$, 1132 cm$^{-1}$, 1242 cm$^{-1}$, 1360 cm$^{-1}$, 1608 cm$^{-1}$.

Alternatively, crystalline form I of abexinostat tosylate may be characterised by the X-ray powder diffraction diagram which includes the 12 significant lines given hereinabove and also by a Raman spectrum having a significant peak at the position 1608 cm$^{-1}$.

Finally, crystalline form I of abexinostat tosylate has also been characterised by solid-state NMR spectroscopy. Significant peaks were observed at 121.2 ppm, 122.1 ppm, 123.5 ppm, 126.0 ppm, 126.8 ppm, 128.2 ppm, 128.9 ppm, 143.4 ppm, 144.6 ppm, 153.8 ppm, 159 ppm, 161.2 ppm and 162.1 ppm.

More specifically, the $^{13}$C CP/MAS (Cross Polarization Magic Angle Spinning) spectra have the following peaks (expressed in ppm ±0.2 ppm):

| Peak no. | Chemical shift (ppm) |
|---|---|
| 1 | 162.1 |
| 2 | 161.2 |
| 3 | 159.0 |
| 4 | 153.8 |
| 5 | 144.6 |
| 6 | 143.4 |
| 7 | 128.9 |
| 8 | 128.2 |
| 9 | 126.8 |
| 10 | 126.0 |
| 11 | 123.5 |
| 12 | 122.1 |
| 13 | 121.3 |
| 14 | 65.9 |
| 15 | 50.6 |
| 16 | 46.9 |
| 17 | 45.0 |
| 18 | 21.9 |

The invention relates also to a process for the preparation of crystalline form I of abexinostat tosylate, which process is characterised in that abexinostat is crystallised from a polar medium in the presence of para-toluenesulphonic acid. Preferably, the polar medium is composed of one or more solvents selected from water, alcohols, ketones and esters, it being understood that:
- "alcohols" means $C_1$-$C_6$ alcohols such as methanol, ethanol, propanol, isopropanol, butanol, isobutanol, pentanol, 2-pentanol, 3-pentanol, isopentanol, hexanol,
- "ketones" means a $C_3$-$C_6$ ketone such as acetone, methyl ethyl ketone, 2-pentanone, 3-pentanone, 3-methyl-2-butanone, 2-hexanone, 3-hexanone, ethyl isopropyl ketone, methyl isopropyl ketone, 2,2-dimethyl-3-butanone,
- "esters" means $C_3$-$C_8$ ester such as ethyl formate, isopropyl formate, ethyl acetate, propyl acetate, isopropyl acetate, butyl acetate, isobutyl acetate, tert-butyl acetate, pentyl acetate, isopentyl acetate, hexyl acetate.

Preferred alcohols are ethanol and isopropanol. Among the preferred solvents preference will also be given to acetone and methyl ethyl ketone among the ketones and to ethyl acetate among the esters.

Alternatively, the polar medium is a binary mixture, one of the constituents of which is water. Even more preferably, the polar medium is a binary mixture selected from: acetone/water, ethanol/water, isopropanol/water and methyl ethyl ketone/water.

In the crystallisation process according to the invention, abexinostat (free base) obtained by any process may be used.

The invention relates also to another process for the preparation of crystalline form I of abexinostat tosylate, in which process the crystallisation is seeded using a very small amount of crystalline form I of abexinostat tosylate.

In this second crystallisation process according to the invention, abexinostat (free base) obtained by any process may also be used.

Obtaining crystalline form I of abexinostat tosylate has the advantage of making it possible to prepare pharmaceutical formulations having a consistent and reproducible composition and having good characteristics of dissolution and stability, which is especially advantageous when the formulations are intended for oral administration. More specifically, use of crystalline form I of abexinostat tosylate is especially valuable in an industrial context in view of its low hygroscopicity.

Crystalline form I of abexinostat tosylate is intended for the treatment of cancer, more especially the treatment of a carcinoma, a tumour, a neoplasm, a lymphoma, a melanoma, a glioma, a sarcoma or a blastoma.

The invention relates also to pharmaceutical compositions comprising, as active ingredient, a tosylate salt of abexinostat, even more especially crystalline form I of abexinostat tosylate, together with one or more appropriate, non-toxic, inert excipients. Among the pharmaceutical compositions according to the invention there may be more especially mentioned those that are suitable for oral, parenteral (intravenous or subcutaneous) or nasal administration, tablets or dragées, granules, sublingual tablets, capsules, lozenges, suppositories, creams, ointments, dermal gels, injectable preparations, drinkable suspensions and chewing gums.

Preference is given to pharmaceutical compositions administered via the oral route.

The useful dosage varies according to the sex, age and weight of the patient, the administration route, the nature of the cancer and any associated treatments; the useful dosage ranges from 20 mg to 480 mg of N-hydroxy-4-{2-[3-(N,N-dimethylaminomethyl)-benzofuran-2-ylcarbonylamino]ethoxy}benzamide per day expressed in terms of the free base.

The Examples hereinbelow illustrate the invention but do not limit it in any way.

EXAMPLE 1

Process for Obtaining Crystalline Form I of Abexinostat Tosylate 1.66 kg of abexinostat (free base) are placed in 9.48 kg of a mixture of isopropanol/water (50/50 weight/weight) at ambient temperature. para-Toluenesulphonic acid monohydrate (0.83 kg) in 2.36 kg of water is added at ambient temperature. The mixture is then heated at 75° C. for 30 minutes before being cooled to 0° C. When crystallisation is complete, the suspension is filtered at 20° C. After drying, crystalline form I of abexinostat tosylate is obtained in a yield of about 85% and with a purity greater than 99%. The solid was characterised by the X-ray powder diffraction diagram, Raman spectrum and NMR spectrum as set out in Examples 3-5 and 6 hereinbelow.

EXAMPLE 2

Process for Obtaining Crystalline Form I of Abexinostat Tosylate (Seeding)

33.9 kg of abexinostat (free base) are placed in 170 kg of a mixture of isopropanol/water (45.6/54.4 weight/weight) at ambient temperature. A solution composed of para-toluenesulphonic acid monohydrate (17.06 kg) in water (24.1 kg) is added. The mixture is then heated at 70-75° C., cooled and seeded with 1.935 kg of crystalline form I of abexinostat tosylate. The suspension is then filtered at 20° C. After drying, crystalline form I of abexinostat tosylate is obtained in a yield of about 86% and with a purity greater than 99%. The solid was characterised by the X-ray powder diffraction diagram, Raman spectrum and NMR spectrum as set out in Examples 3-5 and 6 hereinbelow.

EXAMPLE 3

Crystalline Form I of Abexinostat Tosylate (X-Ray Powder Diffraction Diagram)

Recording of the data was carried out using a PANalytical X'Pert Pro MPD diffractometer with an X'Celerator detector under the following conditions:
Voltage 45 kV, current 40 mA,
Mounting: theta/theta,
Anode: copper,
K alpha-1 wavelength: 1.54060 Å,
K alpha-2 wavelength: 1.54443 Å,
K alpha-2/K alpha-1 ratio: 0.5,
Measurement mode: continuous from 3° to 55° (Bragg's angle 2 theta) in increments of 0.017°,
Measurement time per step: 35.53 s.

The X-ray powder diffraction diagram of form I of abexinostat tosylate obtained according to the process of Example 1 or 2 is expressed in terms of line position (Bragg's angle 2 theta, expressed in degrees ±0.2°), interplanar distance (expressed in Å) and relative intensity (expressed as a percentage relative to the most intense line). The significant lines have been collated in the following table:

| Line no. | Angle 2-theta (degrees) | Interplanar distance (Å) | Relative intensity (%) |
| --- | --- | --- | --- |
| 1 | 6.50 | 13.581 | 75.6 |
| 2 | 9.94 | 8.894 | 58.4 |
| 3 | 11.35 | 7.789 | 19.1 |
| 4 | 12.33 | 7.173 | 23.7 |
| 5 | 14.08 | 6.285 | 33.1 |
| 6 | 18.95 | 4.683 | 100 |
| 7 | 19.61 | 4.526 | 53.9 |
| 8 | 19.96 | 4.449 | 50.9 |
| 9 | 21.08 | 4.215 | 93.5 |
| 10 | 22.82 | 3.897 | 28.5 |
| 11 | 23.61 | 3.768 | 32.6 |
| 12 | 27.05 | 3.296 | 16.0 |

EXAMPLE 4

Crystalline Form I of Abexinostat Tosylate (Crystal Unit Cell)

A saturated solution of abexinostat tosylate in 2,2,2-trifluoroethanol is prepared by stirring a suspension for 24 hours at ambient temperature, followed by filtration. 1 mL of the resulting solution is then poured into a 1.8-mL HPLC vial, to which 0.25 mL of water is added. The solution is maintained at ambient temperature for 75 minutes. After centrifuging and then drying, the solid is isolated for analysis. From among the crystals obtained a crystal of sufficient quality is taken for single-crystal X-ray diffraction analysis. The crystalline structure of the above single crystal was determined using a Bruker Kappa CCD diffractometer equipped with an FR590 generator having a molybdenum anticathode ($\lambda$MoK$\alpha$1=0.7093 Å) with an angular range from 2° to 27.5° in terms of $\theta$. The following parameters were established:
crystal unit cell: triclinic
unit cell parameters: a=10.467 Å, b=14.631 Å, c=20.159 Å, $\alpha$=73.971°, $\beta$=79.040°, $\gamma$=72.683°
space group: P–1
number of molecules in the unit cell: 4
volume of the unit cell: $V_{unit\ cell}$=2813.0 Å$^3$
density: d=1.345 g/cm$^3$.

EXAMPLE 5

Crystalline Form I of Abexinostat Tosylate (Raman Spectrum)

Form I of abexinostat tosylate was characterised by Raman spectroscopy. The spectra were recorded in diffuse reflectance mode (Raman Station 400, PerkinElmer) using a 785 nm laser. The signal was recorded by a CCD detector. The wavelength shift depends on the material and is characteristic of that material, which allows analysis of the chemical composition and of the molecular arrangement of the sample studied. The spectra were acquired with maximum power (100% laser capacity), a spot size of 100 twenty exposures of 2 seconds and a spectral resolution of 2 cm$^{-1}$. The spectral range explored ranges from 0 to 3278 cm$^{-1}$.

Significant peaks were observed at the following positions: 940 cm$^{-1}$, 1088 cm$^{-1}$, 1132 cm$^{-1}$, 1242 cm$^{-1}$, 1360 cm$^{-1}$, 1608 cm$^{-1}$.

EXAMPLE 6

Crystalline Form I of Abexinostat Tosylate (Solid NMR Spectrum)

Form I of abexinostat tosylate was also characterised by solid-state NMR spectroscopy. The $^{13}$C NMR spectra were recorded at ambient temperature using a Bruker SB Avance spectrometer with a 4-mm CP/MAS SB VTN type probe under the following conditions:
Frequency: 125.76 MHz,
Spectral width: 40 kHz,
Magic angle spinning rate of sample: 10 kHz,
Pulse sequence: CP (Cross Polarization) with SPINAL64 decoupling (decoupling power: 80 kHz),
Repetition delay: 10 s,
Acquisition time: 35 ms,
Contact time: 4 ms,
Number of scans: 4096.

An apodisation function ("5 Hz line broadening") is applied to the collected signal before the Fourier transform. The spectra thereby obtained were referenced relative to a sample of adamantane (the highest-frequency peak of adamantane has a chemical shift of 38.48 ppm).

The peaks observed have been collated in the following table (expressed in ppm ±0.2 ppm):

| Peak no. | Chemical shift (ppm) |
| --- | --- |
| 1 | 162.1 |
| 2 | 161.2 |
| 3 | 159.0 |
| 4 | 153.8 |
| 5 | 144.6 |
| 6 | 143.4 |
| 7 | 128.9 |
| 8 | 128.2 |
| 9 | 126.8 |
| 10 | 126.0 |
| 11 | 123.5 |
| 12 | 122.1 |
| 13 | 121.3 |
| 14 | 65.9 |
| 15 | 50.6 |
| 16 | 46.9 |

-continued

| Peak no. | Chemical shift (ppm) |
|---|---|
| 17 | 45.0 |
| 18 | 21.9 |

EXAMPLE 7

Pharmaceutical Composition

Formula for the preparation of 1000 tablets each containing 100 mg of abexinostat (expressed in terms of the base equivalent):

| | |
|---|---|
| Abexinostat tosylate | 143.4 g |
| Lactose monohydrate | 213.1 g |
| Magnesium stearate | 2.5 g |
| Maize starch | 75 g |
| Maltodextrin | 50 g |
| Anhydrous colloidal silica | 1 g |
| Sodium carboxymethylcellulose | 15 g |

EXAMPLE 8

Hygroscopicity

Hygroscopicity of form I of abexinostat tosylate was assessed using dynamic vapor sorption (DVS) technique. 5 to 10 mg of the drug substance test sample were accurately weighed into a DVS sample pan working at 25° C. under controlled humidity. The mass variation was recorded whilst drying under 0 percent RH (relative humidity) and during two subsequent cycles of increasing and decreasing linear variations of relative humidity in the range 0-90 percent RH at a rate of 10 percent per hour. The relative humidity was maintained constant when it reached either 0 or 90 percent RH until the mass variation was less than 0.002 percent per minute within a limit of time of 15 h.

An increase in weight lower than 0.5% was detected by DVS analysis when a sample was exposed to relative humidities from 0% to 90% at 25° C.

The invention claimed is:

1. A crystalline form I of abexinostat tosylate of formula (II):

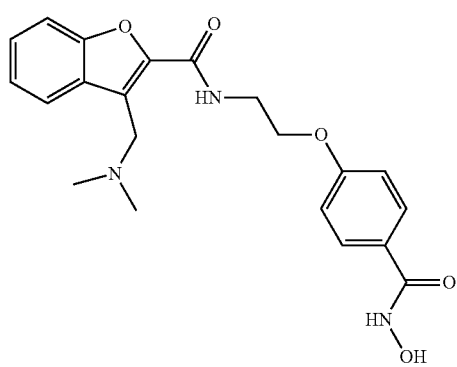

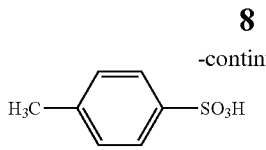

having an X-ray powder diffraction diagram having the following diffraction lines (Bragg's angle 2 theta, expressed in degrees ±0.2°): 6.50, 9.94, 11.35, 12.33, 14.08, 18.95, 21.08, and 27.05.

2. The crystalline form according to claim 1, wherein the crystalline form has an X-ray powder diffraction diagram having the following diffraction lines (Bragg's angle 2 theta, expressed in degrees ±0.2°): 6.50, 9.94, 11.35, 12.33, 14.08, 18.95, 19.61, 19.96, 21.08, 22.82, 23.61, and 27.05.

3. The crystalline form according to claim 1, wherein the crystalline form has the following X-ray powder diffraction diagram:

| Line no. | Angle 2-theta (degrees) | Interplanar distance (Å) |
|---|---|---|
| 1 | 6.50 | 13.581 |
| 2 | 9.94 | 8.894 |
| 3 | 11.35 | 7.789 |
| 4 | 12.33 | 7.173 |
| 5 | 14.08 | 6.285 |
| 6 | 18.95 | 4.683 |
| 7 | 19.61 | 4.526 |
| 8 | 19.96 | 4.449 |
| 9 | 21.08 | 4.215 |
| 10 | 22.82 | 3.897 |
| 11 | 23.61 | 3.768 |
| 12 | 27.05 | 3.296. |

4. The crystalline form according to claim 1, having a Raman spectrum having peaks at 940 cm$^{-1}$, 1088 cm$^{-1}$, 1132 cm$^{-1}$, 1242 cm$^{-1}$, 1360 cm$^{-1}$, and 1608 cm$^{-1}$.

5. A crystalline form I of abexinostat tosylate of formula (II):

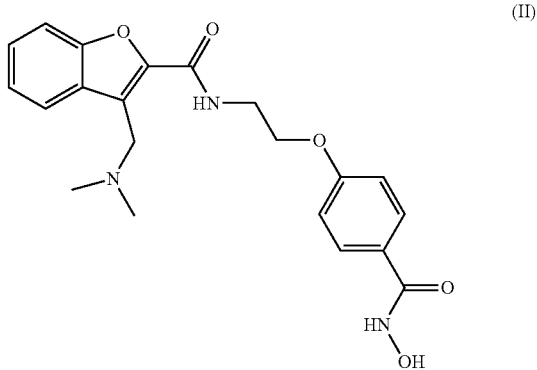 [SMILES: CN(C)Cc1c(C(=O)NCCOc2ccc(C(=O)NO)cc2)oc2ccccc12]

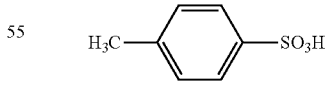

having a Raman spectrum having peaks at the positions 940 cm$^{-1}$, 1088 cm$^{-1}$, 1132 cm$^{-1}$, 1242 cm$^{-1}$, 1360 cm$^{-1}$, and 1608 cm$^{-1}$.

6. The crystalline form according to claim 1, having a solid-state $^{13}$C CP/MAS NMR spectrum having the following peaks (expressed in ppm ±0.2 ppm): 121.2 ppm, 122.1 ppm, 123.5 ppm, 126.0 ppm, 126.8 ppm, 128.2 ppm, 128.9 ppm, 143.4 ppm, 144.6 ppm, 153.8 ppm, 159 ppm, 161.2 ppm, and 162.1 ppm.

7. The crystalline form according to claim 6, wherein the crystalline form has a solid-state $^{13}$C CP/MAS NMR spectrum having the following peaks (expressed in ppm ±0.2 ppm):

| Peak no. | Chemical shift (ppm) |
|---|---|
| 1 | 162.1 |
| 2 | 161.2 |
| 3 | 159.0 |
| 4 | 153.8 |
| 5 | 144.6 |
| 6 | 143.4 |
| 7 | 128.9 |
| 8 | 128.2 |
| 9 | 126.8 |
| 10 | 126.0 |
| 11 | 123.5 |
| 12 | 122.1 |
| 13 | 121.3 |
| 14 | 65.9 |
| 15 | 50.6 |
| 16 | 46.9 |
| 17 | 45.0 |
| 18 | 21.9 |

8. A pharmaceutical composition comprising as active ingredient the crystalline form I of abexinostat tosylate according to claim 1, in combination with one or more pharmaceutically acceptable excipients.

9. A method of treating cancer in a subject in need thereof, comprising administration of an effective amount of the pharmaceutical composition according to claim 8, wherein the cancer is a lymphoma, a melanoma, or a sarcoma.

10. A process for the preparation of crystalline form I of abexinostat tosylate according to claim 1, wherein the abexinostat is crystallised in the presence of para-toluenesulphonic acid in a polar medium.

11. The process according to claim 10, wherein the polar medium is composed of one or more solvents selected from water, alcohols, ketones and esters.

12. The process according to claim 11, wherein the polar medium is a binary mixture, one of the constituents of which is water.

13. The process according to claim 12, wherein the polar medium is a binary mixture selected from: acetone/water, ethanol/water, isopropanol/water and methyl ethyl ketone/water.

* * * * *